United States Patent [19]
Chauffert et al.

[11] Patent Number: 5,635,515
[45] Date of Patent: Jun. 3, 1997

[54] THERAPEUTIC AGENTS FOR THE TREATMENT OF MULTIPLE DRUG RESISTANCE OF CANCERS

[75] Inventors: Bruno Chauffert, Dijon; Philippe Genne, Ahuy; Gilles Gutierrez, Lyon, all of France; Rolland-Yves Mauvernay, Lausanne, Switzerland

[73] Assignee: Debiopharm S.A., Lausanne, Switzerland

[21] Appl. No.: 400,415

[22] Filed: Mar. 3, 1995

Related U.S. Application Data

[63] Continuation of Ser. No. 941,449, filed as PCT/EP92/00408, Feb. 24, 1992 published as WO92/14467, Sep. 3, 1992 abandoned.

[30] Foreign Application Priority Data

Feb. 15, 1991 [CH] Switzerland .................. 0576/91
Dec. 2, 1991 [CH] Switzerland .................. 3522/91

[51] Int. Cl.$^6$ .................................................. A61K 31/44
[52] U.S. Cl. .................................................. 514/305
[58] Field of Search ...................................... 514/305

[56] References Cited

PUBLICATIONS

Chemotherapy of Cancer, 2nd Ed, Carter et al, John Wiley & Sons, N.Y., N.Y., 1981, pp. 90–91.
Molecular Pharmacology, vol. 33, No. 4, Apr. 1988, (US), J. M. Zamora et al.: "Physical–chemical properties shared by compounds that modulate multidrug resistance in human leukemic cells", pp. 454–462, see abstract; pp. 457–458.
Proceedings of the 77th Annual Meeting of the American Association for Cancer Research, Los Angeles, CA, 7–10 May 1986, vol. 27, J. M. Zamora et al.: "Potentiation of Vinca alkaloid (VA) cytotoxicity by quinolines, acridines, indole alkaloids and aromatic amines", p. 395, abstract No.: 1567, see the whole document.
International Journal of Cancer, vol. 46, No.: 1, 15 Jul. 1990, (Lusanne, CH), J.F. Eliason et al.: "Human multi–drug–resistant cancer cells exhibit a high degree of selectivity for stereoisomers of verapamil and quinidine", pp. 113–117, see the whole document.
Tetrahedron Letters, vol. 27, No.: 49, 1986, (GB), R.T. Brown et al.: "Stereospecific synthesis of erythro Cinchona alkaloids from secologanin", pp. 6005–6008, see pp. 6005–6006.

H. Rimpler et al.: "Pharmazeutische Biologie II. Biogene Arzneistoffe", 1990, pp. 437–440; Cinchonae cortex, Georg Thieme Verlag, Stuttgart, DE, see pp. 439–440.
J.E.F. Reynolds et al.: "Martindale—The Extra Pharmacopoeia", 28th edition, 1982, p. 1378, The Pharmaceutical Press, London, GB, see monograph No.: 7786–v: Hydroquinidine hydrochloride.
S. Budavari et al.: "The Merck index", 11th edition, 1989, p. 356, Merck & Co., Rahway, NJ, US, see monograph No.: 2289: Cinchonine.
S. Budavari et al.: "The Merck index", 11th edition, 1989, p. 762, Merck & Co., Rahway, NJ, US, see monograph No.: 4736: Hydroquinidine.
Ann. 1st. Super. Sanita, vol. 21, No.: 3, 1985, (IT), D.C. Warhurst: "New drugs and their potential use against drug–resistant malaria", pp. 327–336, see abstract; pp. 328–329.
Nature, vol. 345, 17 May 1990, (London, GB), C. Newbold: "The path of drug resistance", pp. 202–203, see p. 202.
Annals of Tropical Medicine and parasitology, vol. 69, No.: 4, Dec. 1975 (Liverpool, GB), N.M. Mattock et al.: "The experimental chemotherapy of leishmaniasis. III. Detection of antileishmanial activity in some new synthetic compounds in a tissue culture model"; pp. 449–462, see p. 456.
Therapie, vol. 43, No.: 4, Jun./Jul. 1988, B. Flouvat et al.: "Metabolites de la dihydroquinidine observes apres administration a l'homme d'une formulation a liberation prolongee", pp. 255–261, see the abstract.
J. Chem. Soc. Perkin Trans. I, 1988, M. Ihara et al.: "Total synthesis of hydrocinchonidine and hydrocinchonine via photo–oxygenation of an indole derivative", pp. 1277–1281, see the abstract; schemes 1–4.

*Primary Examiner*—Jerome D. Goldberg
*Attorney, Agent, or Firm*—Pennie & Edmonds

[57] ABSTRACT

Cinchonine, dihydrocinchonine or hydroquinidine are used as multidrug resistance inhibiting substance in the treatment of cancerous tumors by the use of cytotoxic agents. Particularly, cinchonine, dihydrocinchonine or hydroquinidine are used in the preparation of pharmaceutical compositions used in the treatment of cancerous tumors developing the phenomenon of multidrug resistance. Application to the treatment of human cancers.

5 Claims, 3 Drawing Sheets

THERAPEUTIC AGENTS FOR THE TREATMENT OF MULTIPLE DRUG RESISTANCE OF CANCERS

This is a continuation, of application Ser. No. 07/941,449, filed as PCT/EP92/00408, Feb. 24, 1992 published as WO92/14467, Sep. 3, 1992, now abandoned.

TECHNICAL FIELD

The object of the invention is a new therapeutic agent used in the theraputic treatment of cancer tumors, and more particularly, an agent designed for reinforcing the effectiveness of cytotoxic substances used in the treatment of human or animal cancer tumors developing the phenomenon of multiple resistance to anticancer agents (multiple drug resistance: MDR).

BACKGROUND ART

The phenomenon of multiple drug resistance is known, and is not restricted only to anticancer agents. Various explanations have been given to this day, to help understanding the mechanisms involved. Concerning the behavior of the cancer tumor cells, it has been possible to identify several different resistance systems: for example, in relation with the cell membrane permeability, the involvement of a specific glycoprotein (P-gp) has been recognized, but it is accepted that other proteinic factors can be involved.

This phenomenon needs to be addressed in its varied, if not complicated aspects, which makes the investigations aimed at providing proper solutions all the more difficult.

The employment of cytotoxic substances or drugs in the treatment of cancer tumors is confronted with several problems. Firstly, most drugs used for this purpose exhibit a nonspecific inherent toxicity leading to adverse side effects; on the other hand, because of this inherent toxicity, the mounts which can be administered to patients are limited and in numerous cases, the activity needed at the site of the tumors, is not sufficient any more.

Various means have already been proposed for overcoming these problems, such as the use of a vector for the cytotoxic substance, for example through the incorporation into liposomes. In such a case however, though the inherent toxicity of the cytotoxic substance is temporarily masked and hence has limited side effects on the patient, its activity is not always restored at the site of the tumor to the desired level of effectiveness.

Furthermore, should the tumor cells subjected to such a treatment develop the phenomenon of multiple drug resistance—whether this property be innate or acquired—the cytotoxic substance loses almost totally its effectiveness.

Several substances are known to-day which display in vitro an inhibitory activity against MDR: they are mostly noncytotoxic substances, generally of a hydrophobic nature, such as for example alkaloids. In vitro, their concomitant use with a cytotoxic drug appears to be satisfactory, the so-called MDR phenomenon being significantly inhibited at the cellular level, so that the drug is able to fulfil its function unhindered.

The situation is however quite different, when one tries to apply such results to a living body. The substances inhibiting MDR, alkaloids or others, also exhibit an inherent toxicity which limits their administration to beneath a level (serum level) at which the activity desired (MDR inhibition) is already lost. Furthermore, although the cytotoxic substance is administered in its free form or as liposomes for example, it has been found that a limiting factor of importance was the concomitant increase in the inherent toxicity of the cytotoxic drug, due to a significant change in its pharmacological distribution throughout the body. In fact, when confronted with such difficulties, those skilled in the art are left with barely any option, when it comes to treating in vivo cancer tumors which exhibit the phenomenon of multiple drug resistance (MDR). Quinine, which was recently proposed as an MDR inhibiting substance, is a perfect illustration of this situation and its use in human therapy is limited accordingly.

SUMMARY OF THE INVENTION

The invention has the merit of offering a solution which is both novel and particularly effective to the problem discussed above, inasmuch as it makes use of substances having a structure close to that of quinine. Surprisingly however, such substances proved to be more effective at a comparable dose and, at the same time, substantially less toxic than the currently proposed quinine. As was discussed above, the approach of using such alkaloids as substances inhibiting multiple drug resistance in anti-cancer therapy seemingly had little, if any, chance of achieving success.

The object of the invention is the use of cinchonine, of dihydrocinchonine or of hydroquinidine as substances inhibiting multiple drug resistance (MDR) in the treatment of cancer tumors with cytotoxic substances.

Another object of the invention is a pharmaceutical composition for use in the treatment of cancer tumors exhibiting the phenomenon of multiple drug resistance, which contains cinchonine, dihydrocinchonine or hydroquinidine as the substance inhibiting MDR.

DETAILED DESCRIPTION OF THE PREFERRED EMBODIMENTS

Figure 1:
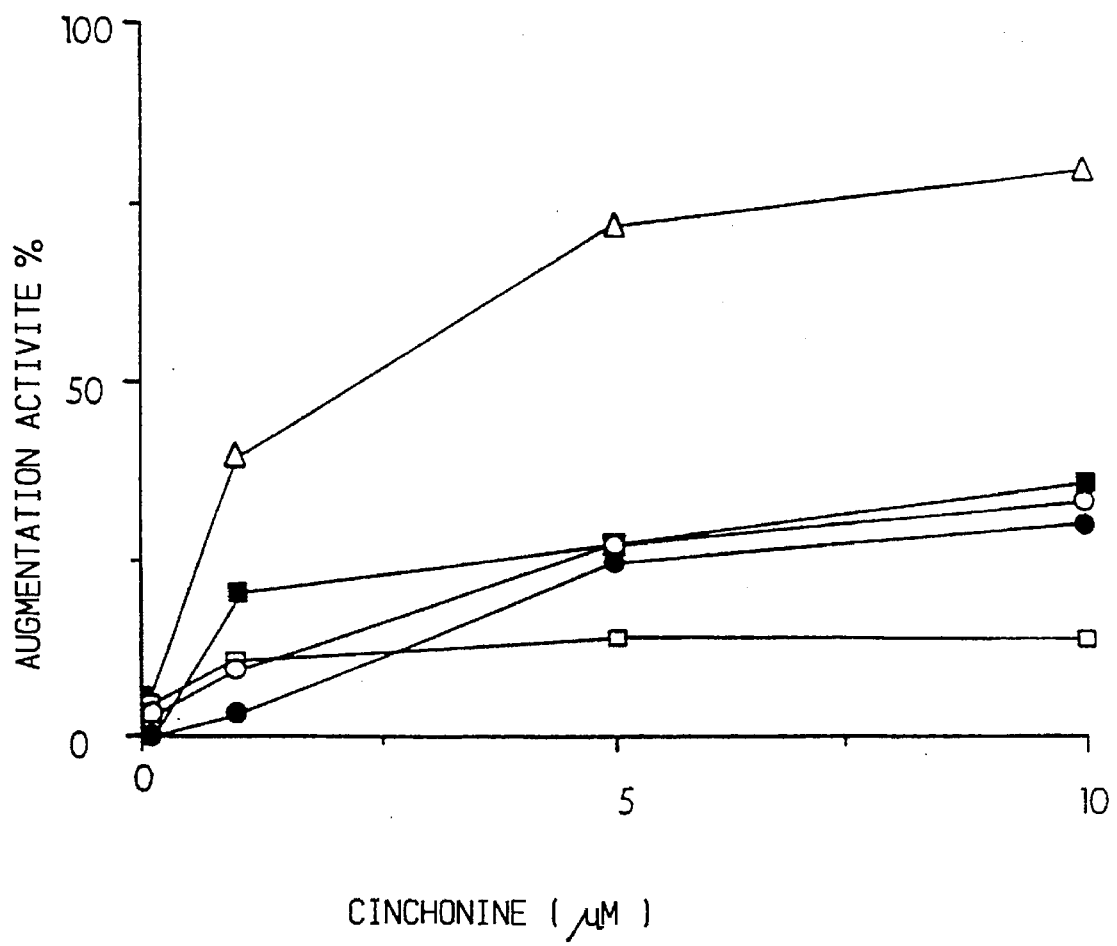
FIG. 1 is a graphical illustration of the activity of certain antimitotic drugs when administered with varying amounts of cinchonine.
Figure 2A:
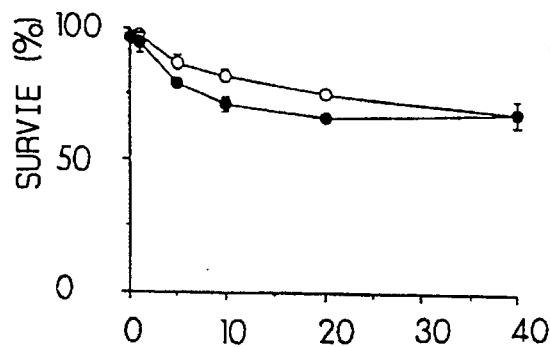
FIGS. 2A, 2B, 2C, and 2D are graphical illustrations of cell survival rate for four different cell rates when doxorubicin is administered with varying amounts of cinchonine or verapamil.
Figure 2B:
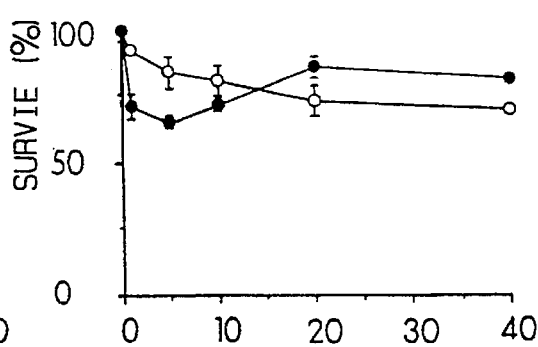
Figure 2C:
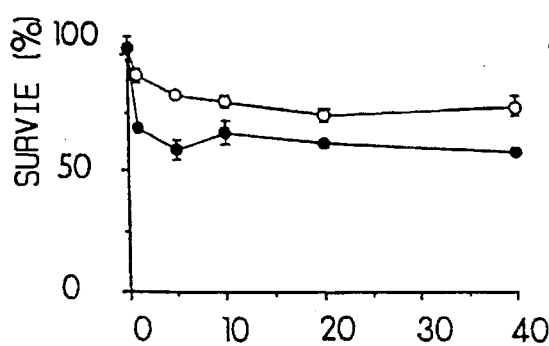
Figure 2D:
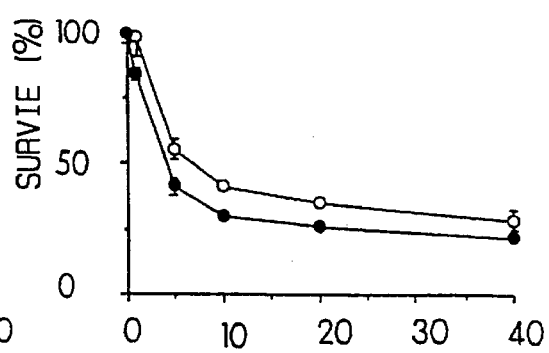

Cinchonine and dihydrocinchonine are known substances belonging to the class of alkaloids, which have been suggested for use as therapeutic agents against malaria. As to hydroquinidine, the compound has been suggested as an antiarrhythmic agent. Both the pharmacology and the toxicity of these substances are known.

According to the invention, cinchonine, dihydrocinchonine and hydroquinidine can be advantageously used in the form of a pharmaceutical composition, dissolved in a medium suitable for parenteral administration, for example by subcutaneous or intramuscular injection or further in the form of a suspension or of tablets designed for oral administration. Further, cinchonine, dihydrocinchonine or hydroquinidine can be associated in such compositions with a particulate vehicle, such as microcapsules, microparticles, nanocapsules or nanoparticles. As an example of a particulate vehicle, one can advantageously use liposomes.

In such pharmaceutical compositions according to the invention, one can use as agent for inhibiting MDR, one of the above-mentioned substances as the only ingredient, such as for example einchonine; one can also use a mixture in various weight ratios of such substances, for example of einchonine and dihydrocinchonine.

Accordingly, a further object of the invention will be a pharmaceutical composition intended for the treatment of cancer tumors, containing as the agent for inhibiting MDR, one or several substances selected from cincho- nine, dihydrocinchonine and hydroquinidine.

Further, it is understood that such substances can be provided in the form of pure stereoisomers or of mixtures of such stereoisomers, or further of pure enantiomers or of mixtures or enantiomers. In the ease of cinchonine or of dihydrocinchonine for example, one can actually recognize different isomers, varying by their configuration at the C8 or C9 carbon.

According to the invention, substances such as cinchonine, dihydrocinchonine or hydroquinidine can be used concomitantly with other substances inhibiting MDR, and more particularly with substances the inhibitory activity of which has already been recognized. In this respect, one can mention, without being limited thereto, one or several known substances selected from amiodarone, quinine, quinidine, cinchonidine, verapamil, cyclosporin A, cephalosporins, biperiden, lidocaine, chlorpromazine, pentazocine, promethazine, potassium canrenoate, amitriptyline, propanolol, demethoxyverapamil, diltiazeme, thioridazine, trifluoperazine, chloroquine, sdbethylene diamine, reserpine, tamoxifen, toremifen, hydrocortisone, progesterone, salbutamol and their acylated derivatives or esters.

According to the invention, the desired inhibitory effect can be obtained with doses at which no adverse side effects are observed with the patients, which could be ascribed to the inherent toxicity of cinchonine, of dihydrocinchonine or of hydroquinidine. Clearly, the optimum therapeutic doses will depend upon the type of tumor being treated, the nature of the cytotoxic agent used concomitantly, the patient treated or other fur- ther factors, within the understanding of those versed in the art.

Cytotoxic substances which are affected by the MDR phenomenon and the effectiveness of which can be advantageously enhanced by the concomitant action of cinchonine, dihydrocinchonine or hydroquinidine are listed hereafter; this recitation is not, however, exhaustive.

They are mostly hydrophobic substances having in common a positively charged nitrogen residue, such as for example the Vinca alkaloids, anthracyclines or similar products, epipodophyllotoxins or anticancer antibiotics. One can mention in particular vincristine, vinblastine, vindesine, vinorelbine, doxorubicin, desoxydoxorubicin, tetrahydropyranyladriamycin, epidoxorubicin, aclacinomycin, demethoxydaunorubicin, daunorubicin, mamsa, mitoxanthrone, bisanthrene, demethoxydaunorubisanthrene, mithramycin, actinomycin D, puromycin, etoposide, tenoposide, emetine, ethidium bromide, cytochalasin, colchicine and taxol.

The invention has made it possible to propose a therapeutic treatment suitable for numerous cancer tumors exhibiting various levels of multiple resistance to anticancer agents (MDR). In this respect, one can mention, amongst others, acute myeloblastic leukaemia, acute lymphoblastic leukaemia, neuroblastoma, small cell lung cancer, ovary cancer, non-Hodgkin malignant lymphoma, diffuse plasmocytoma. These are cancers which can exhibit an induced MDR in response to a treatment with a cytotoxic agent.

One can also treat cancers exhibiting an innate MDR or at least cancer cells characterized by the presence, before any treatment, of the gene corresponding to P-gp (mdr 1) in a relatively high proportion. One can mention, for example, adenocarcinoma of the colon, adenocarcinoma of the kidney, cortico-adrenal carcinoma, pheochromocytoma, children's sarcoma, secondary leukaemia. This recitation is however not exhaustive.

EXAMPLES

The experiments described hereafter illustrate the present invention in a more detailed manner, without however limiting it.

a) Evidence of the inhibitory activity of cinchonine, in vitro a.1. Aliquot portions, each containing 10'000 cells from the DHD/K12/TRb line ("drug resistant cell line"/MDR+), were distributed into series and implanted on slides, 48 hours before the treatment.

A first 60 minute incubation was carried out in HAMF 10 medium, supplemented with additives as follows:

control: - - -
series 0: doxorubicin (DXR) at 10 µg/ml
series 1: DXR (10 µg/ml)+cinchonine (5 µg/ml)
series 2: DXR (10 µg/ml)+quinine (5 µg/ml)
series 3: DXR (10 µg/ml)+verapamil (5 µg/ml)

Series 2 and 3 are used for comparative purposes, since they use substances known to inhibit MDR. A second 75 minute incubation was carried out subsequently in HAMF 10 medium complemented with a renewed portion of the inhibitory substance (series 1 to 3). The semi-quantitative evaluation of the presence of DXR in the cytoplasm of the treated cells was carried out using fluorescence microscopy (double-blind reading) to yield the following results:

| control: 0 | series 0: 0 |
|---|---|
| series 1: +++ | series 2: +++ |
| series 3: +++ | |

0 = no fluorescence
+ = arbitrary unit of fluorescence

It can thus be seen that cinchonine has an inhibitory effect against MDR. This effect is comparable to that found with quinine and verapamil.

a.2. A similar experiment was carried out using aliquot portions each containing 10'000 DHD/K12/ TRb cells, implanted 24 hours before the treatment.

Actual treatment: 72 hour incubation in HAMF 10 medium +10% SVF, in the presence or not of cinchonine, As to the cytotoxic agents, the following ones were used, respectively, at the same concentration: etoposide (VP 16), vincristine. vindesine, mitoxanthrone (MXN) and doxorubicin. Conversely, the cinchonine concentration was varied as follows:

0–0.1–1–5–10 µmol

The survival rates of the implanted cells were evaluated using the blue dye method and converted into % activity of the antimitotic drug. The results obtained are summarized in FIG. 1. They confirm that cinchonine exerts an important inhibitory activity against MDR and enhances the cytotoxic activity of the antimitotic agent being used.

a.3. An experiment similar to the previous one was carried out to check the inhibitory activity of cinchonine, on other colon tumor cell lines in which the product of the expression of the mdr-1 gene and the expression of P-gp 180 had been clearly established.

The selected cells were implanted 24 hours before the treatment, in the proportion of 10'000 cells per well. The actual treatment consists in a 72 hour incubation, in the presence of doxorubicin (DXR) at the same concentration and of the following increasing mounts of cinchonine or verapamil:

0–1–5–10–20–40 μmol

The cell survival rates were determined by means of the blue dye method and the corresponding results are summarized in FIG. 2. The cell lines used were the following:

CACO2-HCT15-SW480-PR0b(DHD/K12/TRb)

The results shown in FIG. 2 are the averages of three determinations. They clearly confirm the inhibitory activity of cinchonine.

b) Evidence of the inhibitory activity of hydroquinidine, in vitro

Aliquot portions, each containing 100'000 cells of the DHD/K12/TRb line ("drug resistant cell line"/MDR+), were distributed in series and implanted on slides 24 hours before the treatment indicated hereafter, the cytotoxic agent being doxorubicin (DXK) containing 3% DXR 14C.

control: - - -
series 0: doxorubicin (DXR) at 10 μg/ml
series 1; DXR (10 μg/ml)+hydroquinidine (15 μg/ml)
series 2: DXR (10 μg/ml)+quinine (15 μμg/ml)
series 3: DXR (10 μg/ml)+verapamil (15 μg/ml)

Series 2 and 3 are used for comparative purposes, since they use substances which are known to inhibit MDR. After a two hour incubation, Followed by three successive two hour washings with PBS-BSA, trypsinization and cell counting, the intracellular radioactivity was measured using a β-ray counter.

The amount of intracytoplasmic doxorubicin directly associated with the inhibitory effect of the tested substance was deduced from these measurements. The results are summarized hereafter:

| Series N° | Agent | Radioactivity |
|---|---|---|
| 0 | DXR only | 200 cpm |
| 1 | DXR + hydroquinidine | 875 cpm |
| 2 | DXR + quinine | 850 cpm |
| 3 | DXR + verapamil | 1050 cpm |

It can thus be seen, that hydroquinidine exerts a significant inhibitory effect on MDR. This effect is at least comparable to that found with quinine.

c) Evidence of the inhibitory activity of cinchonine, ex vivo c.1. Each one of the two following inhibitory substances was administered by intravenous injection to rats, in groups of three, at their maximum nontoxic doses:

cinchonine: 50 mg/kg (1)
quinine: 40 mg/kg (2)

One hour after the IV injection, samples of blood were drawn directly from the heart of each animal. The same treatment was applied to control rats, which had received no treatment.

c.2. Aliquot portions, each containing 10'000 DHD/K12/TRb cells (see a.1), were implanted 48 hours before the actual treatments indicated hereafter, the cytotoxic agent being doxorubicin (DXR):

control: - - -
series 0: DXR (10 μg/ml)+serum of control rats
series 1: DXR (10 μg/ml)+serum of rats (1)
series 2: DXR (10 μg/ml)+serum rats (2)

After a first one hour incubation, 3 successive washings were carried out using HAMF 10, and then a second one hour incubation of the washed cells was carried out in the presence of only a renewed portion of corresponding serum. The semi-quantitative evaluation of the DXR retention by the treated cells was performed by fluorescence microscopy (double-blind reading), to yield the following results:

| control: 0 | Series 0: 0 |
|---|---|
| series 1: +++ | Series 2: ++ |

0 = absence of fluorescence
+ = arbitrary fluorescence unit

It can be seen that cinchonine is at least as effective in vivo for inhibiting MDP, as quinine is.

d) Evidence of the inhibitory activity of hydroquinidine, ex vivo d.1. The two following inhibitory substances were administered by intraperitoneal injection to rats, in groups of three, in the following doses:

hydroquinidine: 75 mg/kg (1)
quinine: 75 mg/kg (2)

One hour after the IP injection, blood samples were drawn directly from the heart of each animal. The same treatment was applied to the control rats, which had received no treatment.

d.2. Aliquot portions, each containing 100'000 DHD/K12/TRb cells (see a.1), were implanted 24 hours before the actual treatment, as indicated hereafter, the cytotoxic agent being doxorubicin (DXR) containing 3% DXR 14C.

control: - - -
series 0: DXR (15 μg/ml)+serum of control rats
series 1: DXR (15 μg/ml)+serum of rats (1)
series 2: DXR (15 μg/rnl)+serum of rats (2)

After two hours of incubation followed by three successive washings using PBS-BSA, trypsinization and cell counting, the intracellular radioactivity was measured using a β-ray counter.

The amount of intracytoplasmic doxorubicin directly associated with the inhibitory effect of the tested substance was deduced from these measurements. The results are summarized below:

| Series N° | Agent | Radioactivity |
|---|---|---|
| 0 | DXR only | 250 cpm |
| 1 | DXR + hydroquinidine | 750 cpm |
| 2 | DXR + quinine | 500 cpm |

It can be seen that for a same serum concentration of the inhibitory substance, the intracytoplasmic DXR level in series 1 (DXR+hydroquinidine) is 3 times higher than in series 0 (DXR only); also, this level is approximately 1.5 times higher than in series 2 (DXR+quinine).

e) Comparison of the potency of cinchonine as inhibitor, with that of quinine, in ex vivo experimentation e.1. Each one of the three following inhibitory substances was administered by intraperitoneal injection to rats, in groups of three, in the following doses:

cinchonine: 75 mg/kg (1)
cinchonine: 100 mg/kg (2)
quinine: 75 mg/kg (3)

quinine: 100 mg/kg (4)*

*2 rats of the 3 died

One hour after the IP injection, blood samples were drawn directly from the heart of each animals. The same treatment was applied to the control rats, which had received no treatment.

e.2. Aliquot portions, each containing 100'000 DHD/K12/TRb cells (see a.1), were implanted 24 hours before the actual treatment in the presence of the cytotoxic agent (doxorubicin (DXR) containing 3% DXR 14C).

control: - - - series 0: DXR (5 µg/ml)+serum of control rats series 1: DXR (5 µg/ml)+serum of rats (1)

series 2: DXR (5 µg/ml)+serum of rats (2)

series 3: DXR (5 µg/ml)+serum of rats (3)

series 4: DXR (5 µg/ml)+serum of rats (4)

After two hours of incubation, followed by three successive washings using PBS-BSA, trypsinization and cell counting, the intracellular radioactivity was measured using a $\beta$-ray counter.

Figure 3:
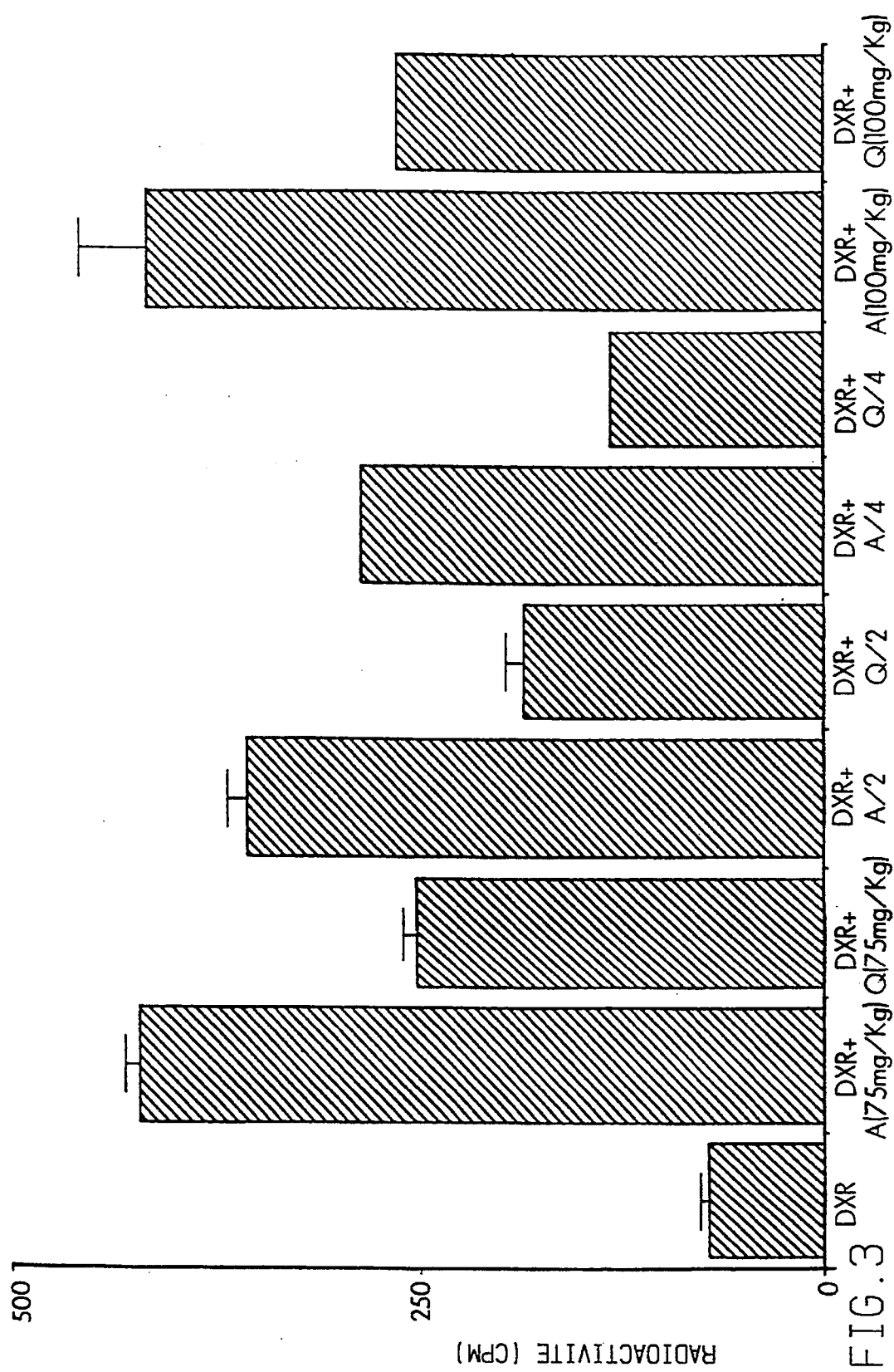
FIG. 3 is a graphical illustration of the amount of intracellular radioactivity, indicative of intracytoplasmic doxorubicin, when doxorubicin was administered with varying amounts of cinchonine or quinine.

The amount of intracytoplasmic doxorubicin directly associated with the inhibitory effect of the tested substance was deduced from these measurements. The results are summarized in FIG. 3.

It can be seen that for a same serum concentration of the inhibitory substance, the intracytoplasmic DXR level in series 1 (DXR+cinchonine) is 6 times higher than in series 0 (DXR only); also, this level is approximately 2 times higher than in series 3 (DXR+quinine), even after a twofold or a fourfold dilution of the sera.

It can further be seen that cinchonine is clearly less toxic than quinine is: for an IP injection of 100 mg/kg, two animals out the three died after the quinine injection.

e.3. A similar experiment was carried out, but using a different cell line: K 562/ADM (myelogenous leukaemia cell line).

It was confirmed that in this case also, cinchonine exhibits a higher inhibitory activity than quinine does.

f) Comparison of the potency of cinchonine as inhibitor, with that of quinine, using an in vivo experimentation 1'000'000 DHD/K12/TRb cells were administered per rat by intraperitoneal injection at day 0, in order to induce a peritoneal carcinomatosis of colic origin, used as the experimental model.

On day 1, free doxorubicin (DXR) and an inhibitory substance were administered simultaneously by intraperitoneal injection using an aqueous 5% glucose solution, in the following amounts:

group I: DXR/quinine: 0.5 mg/kg of DXR and 80 mg/kg of quinine, group 2: DXR/cinchonine: 0.5 mg/kg of DXR and 80 mg/kg of cinchonine group 3: DXR (05 mg/kg)

group 4: control

Each group included 5 rats and they were sacrificed on day 27. After autopsy, the tumor nodules were weighed separately for each animal. The values given hereafter are the averages for the 5 animals of each group.

group 1: 0.2 g (±0.2)

group 2: 0.1 g (±0.1)

group 3: 4.8 g (±1.2)

group 4: 5.0 g (±1.2)

It can thus be seen, that quinine and cinchonine inhibit significantly the resistance of tumors treated by means of doxorubicin. At the same dose. cinchonine is more potent than quinine in this type of experimentation; an additional advantage is the lower toxicity of cinchonine as was shown above.

What is claimed is:

1. A method for treating a patient suffering from multiple drug resistance, which comprises administering to said patient a compound comprising cinchonine and/or hydroquinidine in an amount effective to inhibit the multiple drug resistance of said patient.

2. The method of claim 1 which further comprises administering the compound in the form of a pure stereoisomer, a pure enantiomer, or a mixture of such stereoisomers or enantiomers.

3. The method of claim 1 which further comprises selecting the compound to be administered to be hydroquinidine.

4. The method of claim 1 which further comprises selecting the compound to be administered to be cinchonine.

5. The method of claim 1 wherein cinchonine and hydroquinidine are administered in combination.

* * * * *

UNITED STATES PATENT AND TRADEMARK OFFICE
CERTIFICATE OF CORRECTION

PATENT NO. : 5,635,515

DATED : June 3, 1997

INVENTORS : Chauffert et al.

It is certified that error appears in the above-identified patent and that said Letters Patent is hereby corrected as shown below:

Title page at [73] Assignee: after the first named Assignee insert --Institut National de la Santé et de la Recherche Médicale (INSERM), Paris Cédex, France, and Patrinove, Lyon, France--.

Signed and Sealed this

Sixteenth Day of December, 1997

Attest:

BRUCE LEHMAN

*Attesting Officer*  *Commissioner of Patents and Trademarks*